US011331536B1

(12) United States Patent
Wood

(10) Patent No.: US 11,331,536 B1
(45) Date of Patent: May 17, 2022

(54) ISOKINETIC ROTATIONAL TESTING, EVALUATION AND TRAINING SYSTEM

(71) Applicant: Kelly Wood, Daniel Island, SC (US)

(72) Inventor: Kelly Wood, Daniel Island, SC (US)

( * ) Notice: Subject to any disclaimer, the term of this patent is extended or adjusted under 35 U.S.C. 154(b) by 89 days.

(21) Appl. No.: 16/862,647

(22) Filed: Apr. 30, 2020

(51) Int. Cl.
*A63B 23/08* (2006.01)
*A63B 21/002* (2006.01)
(Continued)

(52) U.S. Cl.
CPC .......... *A63B 23/085* (2013.01); *A61B 5/1124* (2013.01); *A63B 21/002* (2013.01);
(Continued)

(58) Field of Classification Search
CPC ........ A63B 21/00058; A63B 21/00061; A63B 21/00065; A63B 21/00069; A63B 21/00076; A63B 21/002; A63B 21/0023; A63B 21/02; A63B 21/04; A63B 21/0407; A63B 21/0414; A63B 21/0421; A63B 21/0428; A63B 21/0435; A63B 21/0442; A63B 21/055; A63B 21/0552; A63B 21/0555; A63B 21/0557; A63B 21/062; A63B 21/0624; A63B 21/0626; A63B 21/0628; A63B 21/063; A63B 21/0632; A63B 21/15; A63B 21/151; A63B 21/154; A63B 21/22; A63B 21/4027; A63B 21/4029; A63B 21/404033; A63B 21/4034; A63B 21/4035; A63B 21/4039; A63B 21/4045; A63B 21/4047; A63B 21/4049; A63B 22/14; A63B 22/18; A63B 2022/185; A63B 23/08; A63B 23/085; A63B 24/0062; A63B 69/0057; A63B 69/0069; A63B 69/0062; A63B 71/0054; A63B 71/0619; A63B 71/0622; A63B 2071/0063; A63B 2071/0072; A63B 2071/065; A63B 2071/0658; A63B 2208/0228; A63B 2208/0233; A63B 2220/10; A63B 2220/16; A63B 2220/20; A63B 2220/24; A63B 2220/50; A63B 2220/51; A63B 2220/52;
(Continued)

(56) References Cited

U.S. PATENT DOCUMENTS 3,774,597 A * 11/1973 Root .................... A61H 1/0237
601/27
3,911,907 A * 10/1975 Smith, Jr. ................ A61H 1/02
482/1
(Continued)

*Primary Examiner* — Gary D Urbiel Goldner
(74) *Attorney, Agent, or Firm* — Sandy Lipkin

(57) ABSTRACT

An isokinetic rotational exercise device provides for training and collection of information of a knee joint as it rotates. The isokinetic rotational exercise device includes vertical supports attached to a base frame that provides for an inclusion of rotational foot plates. The rotational foot plates are connected to cables of a pulley system that allows for an ability to add resistance of free weights and resistance tubing. Bottoms of the rotational foot plates include sensors to measure rotational degree, and the corresponding information is sent to a processor for display on a monitor on the isokinetic rotational exercise device or to an external device. A degree of force used to turn the rotational foot plates when the resistance is added is data collectable through force sensors in the cables of the pulley system.

11 Claims, 17 Drawing Sheets

(51) Int. Cl.
*A63B 24/00* (2006.01)
*A61B 5/11* (2006.01)
*A63B 71/06* (2006.01)
*A63B 21/00* (2006.01)

(52) U.S. Cl.
CPC ........ *A63B 21/154* (2013.01); *A63B 21/4034* (2015.10); *A63B 21/4035* (2015.10); *A63B 21/4039* (2015.10); *A63B 21/4049* (2015.10); *A63B 24/0062* (2013.01); *A63B 71/0622* (2013.01); *A63B 2071/0658* (2013.01); *A63B 2220/24* (2013.01); *A63B 2220/51* (2013.01); *A63B 2225/093* (2013.01)

(58) Field of Classification Search
CPC ............ A63B 2220/58; A63B 2220/80; A63B 2220/83; A63B 2220/833; A63B 2225/02; A63B 2225/09; A63B 2225/093; A63B 2225/50; A63B 2225/52; A63B 2225/54
See application file for complete search history.

(56) References Cited

U.S. PATENT DOCUMENTS

| | | | | |
|---|---|---|---|---|
| 4,200,282 A * | 4/1980 | Agyagos | A63B 17/00 | 482/147 |
| 4,515,363 A * | 5/1985 | Schleffendorf | A63B 21/155 | 482/100 |
| 4,625,959 A * | 12/1986 | Schleffendorf | A63B 21/155 | 482/100 |
| 4,659,084 A * | 4/1987 | Vuick | A63B 69/3621 | 473/264 |
| 5,054,852 A * | 10/1991 | Tholkes | A61G 5/14 | 297/172 |
| 5,306,220 A * | 4/1994 | Kearney | A63B 23/00 | 482/104 |
| 5,597,375 A * | 1/1997 | Simonson | A63B 23/1254 | 482/100 |
| 5,884,935 A * | 3/1999 | Tholkes | A61G 5/14 | 280/657 |
| 5,941,807 A * | 8/1999 | Cassidy | A63B 23/0233 | 482/146 |
| 6,280,368 B1 * | 8/2001 | Liao | A63B 22/14 | 482/146 |
| 6,440,046 B1 * | 8/2002 | Tholkes | A61G 5/14 | 280/250.1 |
| 9,028,369 B2 * | 5/2015 | Hjort | A63B 21/4034 | 482/8 |
| 10,322,764 B2 * | 6/2019 | Thomas | B62J 9/21 | |
| 2007/0259763 A1 * | 11/2007 | McKeown | A63B 22/14 | 482/146 |
| 2009/0253561 A1 * | 10/2009 | Centrella | A63B 21/154 | 482/125 |
| 2010/0078536 A1 * | 4/2010 | Galvin | B64D 11/00152 | 248/231.51 |
| 2015/0045193 A1 * | 2/2015 | Morton | A63B 23/085 | 482/123 |
| 2016/0236025 A1 * | 8/2016 | Henan | A63B 23/03508 | |
| 2017/0152990 A1 * | 6/2017 | Kielland | G03B 17/561 | |
| 2017/0165517 A1 * | 6/2017 | Morton | A63B 21/4035 | |
| 2019/0001183 A1 * | 1/2019 | Liao | A63B 21/00181 | |
| 2020/0009420 A1 * | 1/2020 | Sinegal | A63B 21/151 | |

* cited by examiner

ISOKINETIC ROTATIONAL TESTING, EVALUATION AND TRAINING SYSTEM

BACKGROUND OF THE INVENTION

Field of the Invention

The field of this invention relates generally to the field of exercise machines and more particularly toward an isokinetic rotational testing, evaluation and training System integrated into an exercise apparatus used for training and rehabilitation exercises.

Description of the Prior Art

The system and device of the instant application is an improvement over U.S. Provisional Pat. App. No. 62/979,090 on Feb. 20, 2020 by the instant inventor among others. The instant invention seeks to make several improvements over the prior design which are described herein.

The present disclosure provides for an isokinetic rotational testing, evaluation and training system that can be used by a user, as well as a therapist or trainer to assist a user. The isokinetic rotational testing, evaluation and training system can be used for a large variety of activities and training/rehabilitation exercises, which includes general sports training for isokinetic evaluation, testing and training. It is ideal for athletes who want to improve strength, speed, and stabilization in the lower body kinetic chain. The user can exercises using a closed kinetic chain as well as the open kinetic chain. It is great for basketball, football, baseball, tennis, golf, hockey, softball, soccer, volleyball. It is an excellent rehabilitation tool for athletes and the elderly because the equipment allows the user to train in a range equivalent to one pound up to 90 pounds of free weight resistance.

Many people are weak after an injury and they need to start with very light weights. Additionally, it is a great tool for the elderly because it fits into the "slip and fall risk category" in that they have to engage their brain in order to find their foot as they get onto to the machine. This mimics a potential fall risk. Accordingly, the machine qualifies as a tool to help the elderly. With the system, the user and/or his or her trainer are able to progress the subject with light resistance. By contrast, most exercise equipment starts with 10 pounds whereas this system and machine allows the user to start with just 1 pound of resistance. For rehabilitation purposes, utilizing this system, the user and/or his or her trainer are able to assess, identify and strength train weak muscles in the knees, hips and low back. The system helps a therapist to identify weak muscles and compensation patterns at the ankle, knee, hip and trunk.

Once weakness or muscle compensations are identified, the user and/or his trainer are able to strengthen the key muscles in the kinetic chain allowing for better gait mechanics. For athletes, the short quick movements, called terminal flicks, speed up the firing of the neural pathways, thereby improving speed and strength at the joint.

It is the object of the instant invention to improve over the prior invention through an improved foot restraint system, an improved knee support system and the introduction of a monitor and sensors to read and collect data wherein the monitor is attached to a height adjustable handrail that provides improved stability to the user.

SUMMARY OF THE INVENTION

The basic embodiment of the present invention teaches an exercise apparatus for the training and rehabilitation comprising: a base frame; a vertical support extending upward from said base frame; a top frame member attached to said vertical support and being substantially parallel to said base frame; a rotating foot system attached to said base frame; a pulley system attached to said rotating foot system; a knee support system attached to said vertical support that is situated above and substantially parallel to said rotating foot system; a hand rail attached to said top frame member; and a monitor attached to said hand rail.

The above embodiment can be further modified by defining that said rotating foot system further comprises: a base plate affixed to said base frame for each foot of a user; a foot plate connected to base plate; at least one strap to secure the foot of a user to said foot plate; a shaft extending downwardly from said foot plate through said base plate;

a sensor connected to said shaft wherein said sensor detects the angle of rotation data of said foot plate when rotated by a user.

The above embodiment can be further modified by defining that said sensors sends said angle of rotation data collected when used by a user to a processor.

The above embodiment can be further modified by defining that said processor utilizes said data sent thereto and is then displayed on said monitor or to an external device.

The above embodiment can be further modified by defining that protruding members are connected to said pulley system in order to receive free weights in order to add resistance to said pulley system.

The above embodiment can be further modified by defining that resistance bands are added to said pulley system in order add resistance to said pulley system.

The above embodiment can be further modified by defining that force sensors are included in the cables of said pulley system wherein said force sensors send resistance to data to a processor.

The above embodiment can be further modified by defining that said processor utilizes said data sent thereto and is displayed on said monitor or sent to an external device.

The above embodiment can be further modified by defining that said knee support system further comprises: a removable bracket that is attachable to said vertical support, said removable bracket having a substantial t-shape with a long member that is situated above said rotating foot system and is substantially parallel thereto and a short member that is perpendicular to said long member and wherein said short member is the portion that releasably attaches to said vertical support; a support pad corresponding to each of the front of each knee of a user situated along said long portion; a pair of adjustable pads extending outward from said long portion toward each knee of the user such that said pair of adjustable pads surrounds and supports each knee of the user wherein said pair of adjustable pads are adjustable in the plane toward and away from each knee of the user for support of each knee of the user.

The above embodiment can be further modified by defining that said pair of adjustable pads are contoured and padded for comfort.

The above embodiment can be further modified by defining that said bracket is adjustable in a vertical direction to accommodate the height of the calf of the user.

The above embodiment can be further modified by defining that said bracket is adjustable in a horizontal direction to accommodate the length of the thigh of the user.

The above embodiment can be further modified by defining that said handrail is adjustable in the vertical direction to accommodate the height of the user.

The above embodiment can be further modified by defining that said monitor is rotatably adjustable 360 degrees so that it can be viewed either by the user or a trainer.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF A PREFERRED EMBODIMENT

Figure 1:
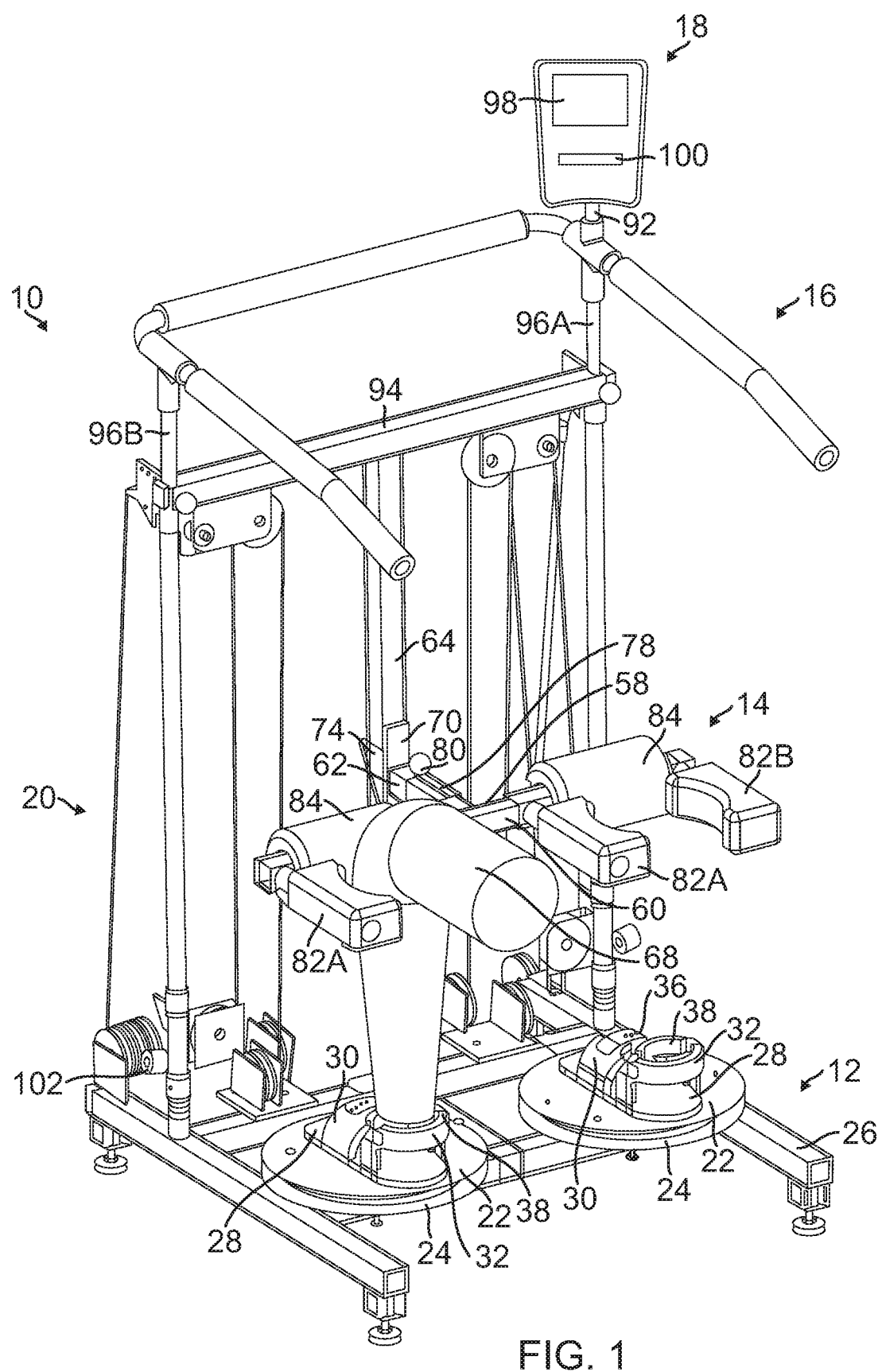
FIG. 1 is a front perspective view of the apparatus of the instant invention with an exemplary knee shown.
Figure 2:
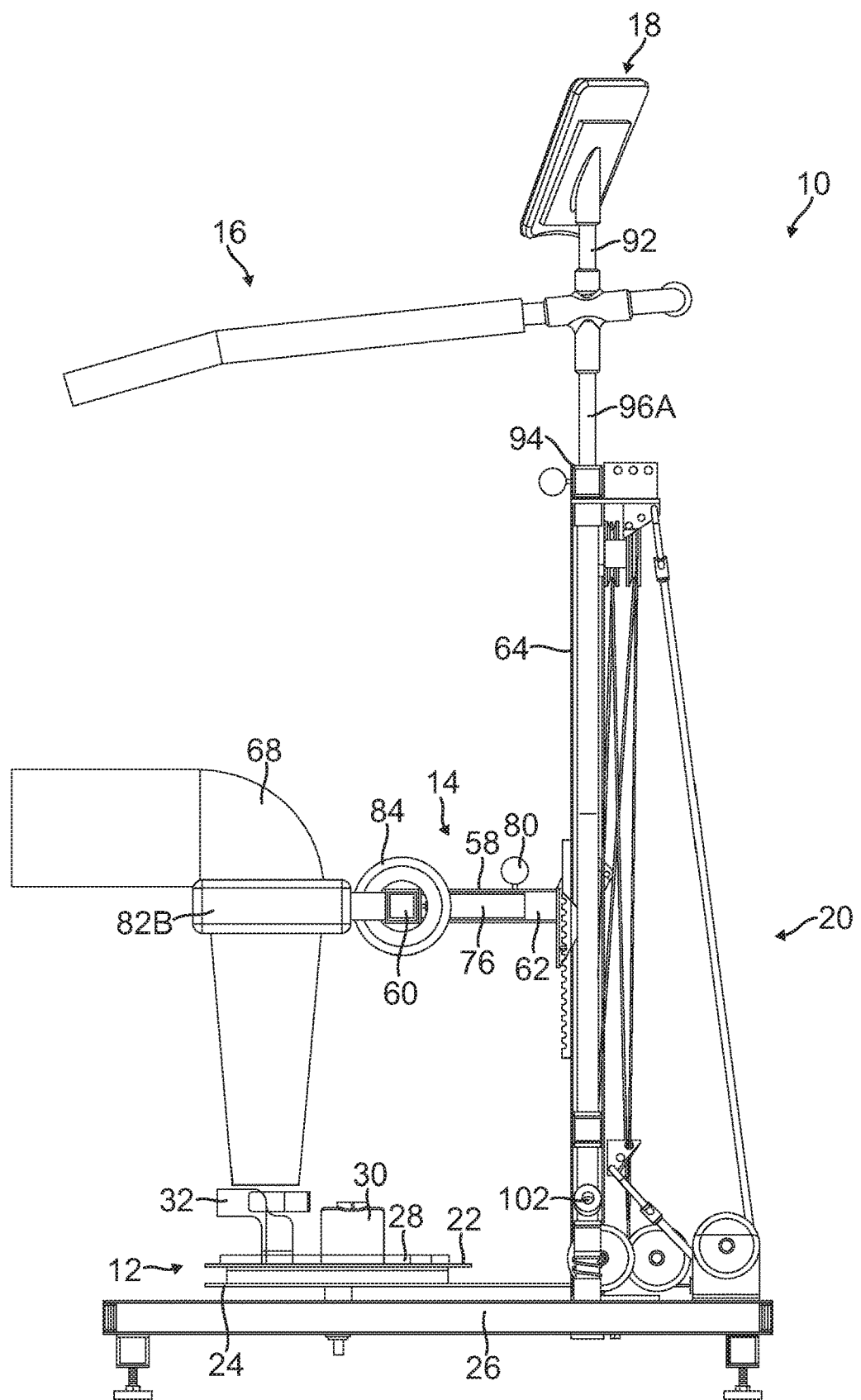
FIG. 2 is a side view of the apparatus of the instant invention with an exemplary knee shown.

Turning to the drawings, the preferred embodiment is illustrated and described by reference characters that denote similar elements throughout the several views of the instant invention.

The preferred embodiment of the instant invention provides for an isokinetic rotational testing, evaluation and training system apparatus 10 which is comprised of a foot plate system 12, a knee support system 14 and a hand rail system 16 with monitor 18. The isokinetic rotational testing, evaluation and training System 10 retains unchanged the back pulley system 20 at a rear portion of the apparatus 10.

Turning to the improved foot plate system 12, which can be seen in FIGS. 1-6, 11 and 16, the foot plate system 12 is comprised of one foot plate 22 for each foot, which as illustrated has a circular shape, but it is to be understood that it is not limited to this shape. Each foot plate 22 is provided on top of and secured to a base plate 24, such that the foot plate 22 can rotate with respect to the base plate 24 and the base frame 26 of the apparatus 10, as will be further described below.

An affixed sole 28 is provided on top of each foot plate 22. Affixed to each sole 28 is a securing foot strap 30 and a securing ankle strap 32. The securing foot strap 30 and securing ankle strap 32 are designed for quick engagement through the use of pins 34 and holes 36 on the straps 30, 32 that allow for an adjustable snug fit depending on the size of the foot of the user. Padding 38 is supplied on the inner portions of the straps 30, 32 for comfort.

When a user turns his foot on the foot plate 22, the foot plate 22, base, plate 24, and the sole of the boot 28 all turn in the same direction with respect to the base frame 26. Sensors 40 attached to rods 42 on the underside of the foot plate system 12 (See FIG. 16) wherein the sensors 40 are in communication with the monitor 18 which can read and display information regarding the angle of rotation of the foot of the user.

In general operation, a rotational sensor 40 will be placed under each rotating foot plate 22 to detect how far the foot plate 22 rotates from an initial position. The foot plate 22 can rotate in either direction and as far in either direction as needed for use of the apparatus 10. As each foot plate 22 is rotated, the sensor 40 under each plate 22 will read the angle that the foot plate 22 rotates in degrees as measured from the initial position. This information will be sent from each sensor 40 to a processor which will process the information, and then relay this processed information to a video output 98 on the monitor 18 for the user to see. There will be two foot plates 22 on the exercise equipment, and so two sensors 40. The data from both sensors 40 will be sent to one processor. The data from the sensors 40 can be processed in any way that the user finds useful, which can include, but is not be limited to. the maximum angular amounts to which each foot plate 22 is rotated. The video output device 98 will be placed in a place that is convenient for the user to view. This video output device 98, such as an LCD screen, may have buttons 100 to modify the processed information and/or modify the way the data is displayed. The processed information may also be sent to other endpoints by any means including, but not limited to, devices connected by hardwire or wireless devices.

Each foot plate 22 will have a connected shaft 42 extending vertically downward below the foot plate 22 through the base frame 26 of the exercise apparatus 10. The vertical shaft or rod 42 will be connected at its top to the bottom center of the foot plate 22 so that the shaft 42 rotates with the foot plate 22. The rotational sensor 40 will be connected to the bottom end of the vertical shaft 42 so that the sensor 40 will detect how far the shaft 42, and so the foot plate 22, rotates.

As the subject moves, the therapist can document at what degree compensations occur such as toes curling downward, a foot that supinates, toes dorsi flexing or fore foot pronation. This process of identifying compensations can help the therapist in the right direction in a rehabilitation process.

Figure 3:
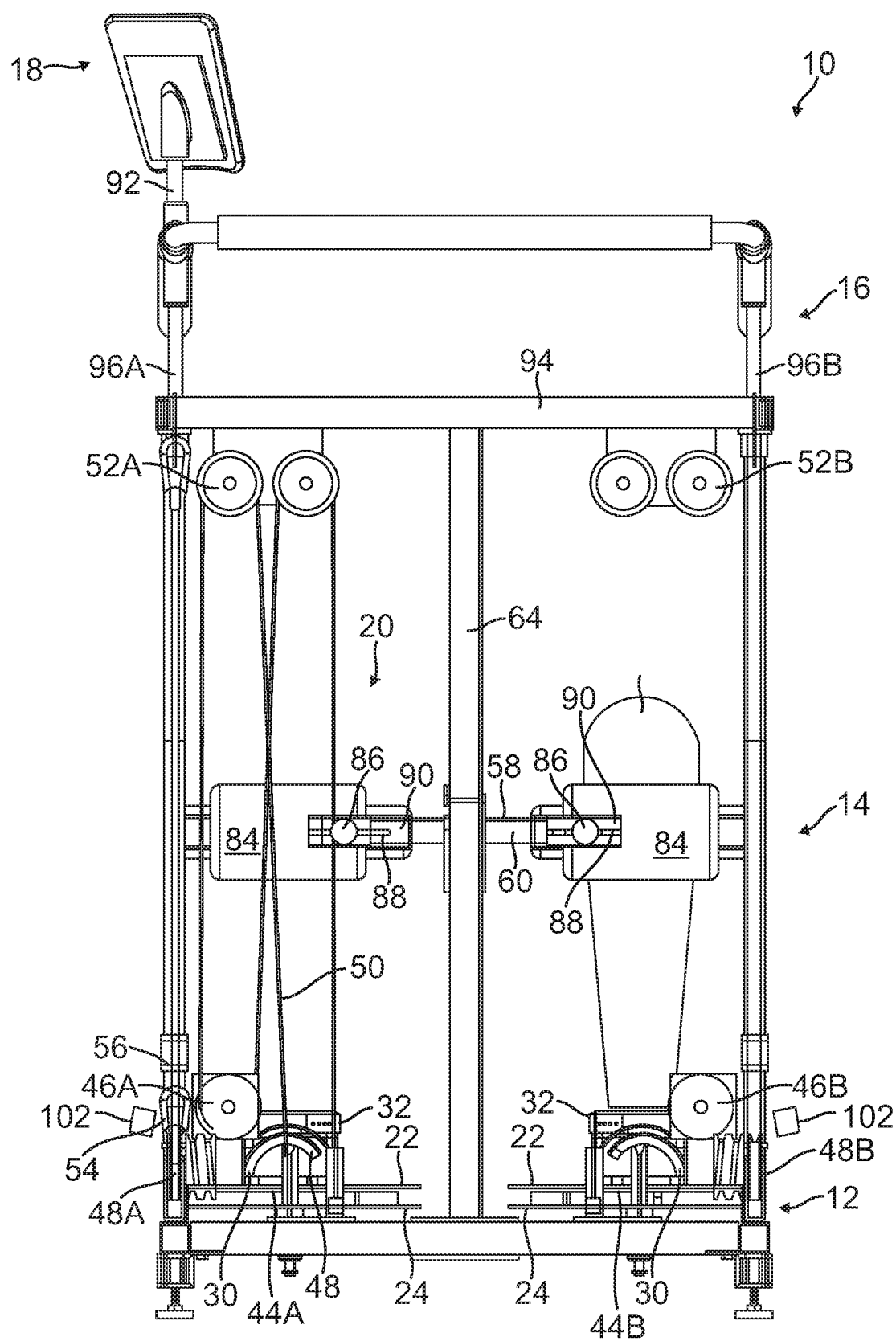
FIG. 3 is a back view of the apparatus of the instant invention with an exemplary knee shown.
Figure 4:
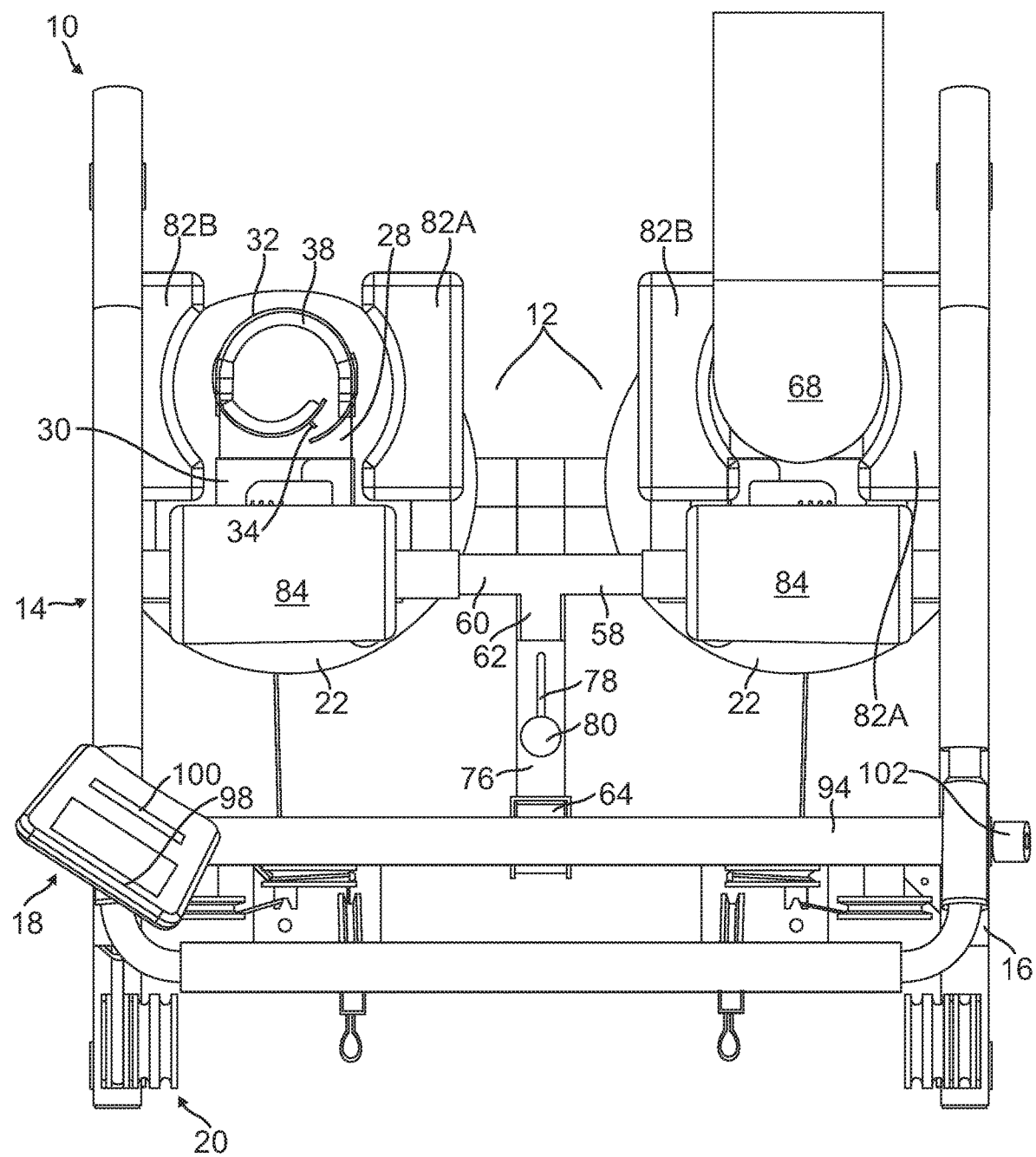
FIG. 4 is a top view of the apparatus of the instant invention with an exemplary knee shown.
Figure 5:
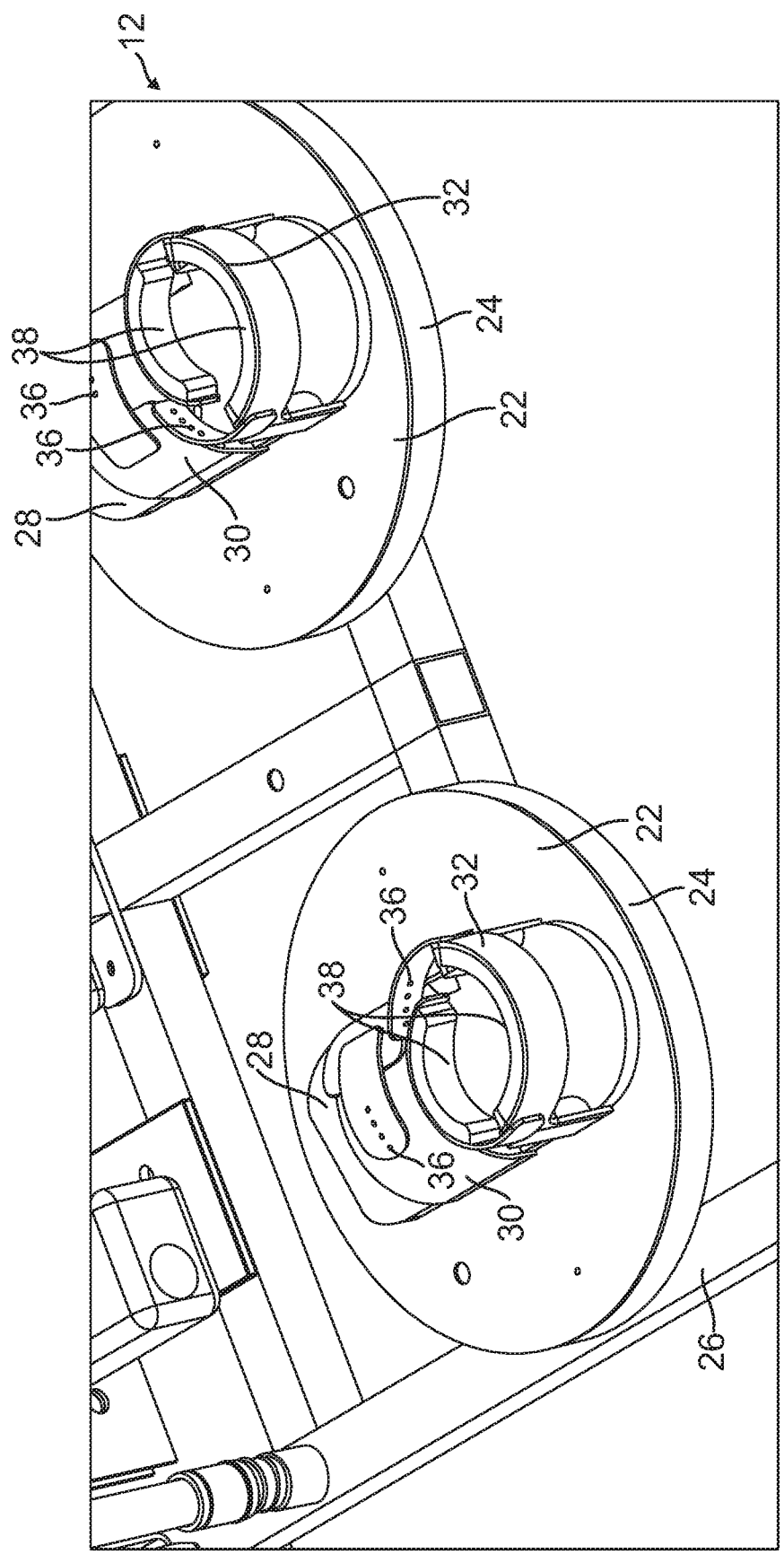
FIG. 5 is a close up top view of the foot plates and foot restraints of the apparatus of the instant invention.
Figure 6:
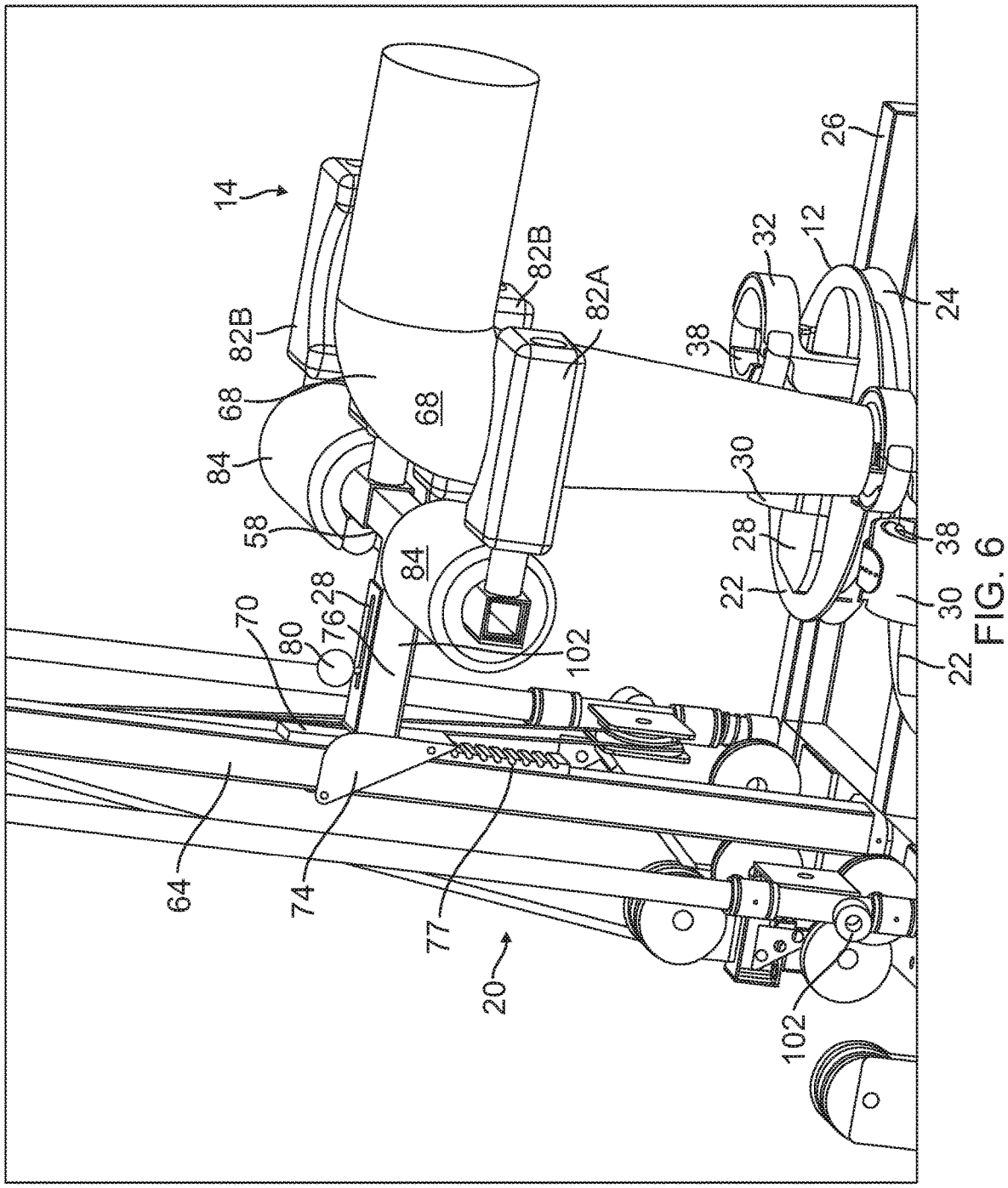
FIG. 6 is a side perspective view of the knee support of the apparatus of the instant invention.
Figure 7:
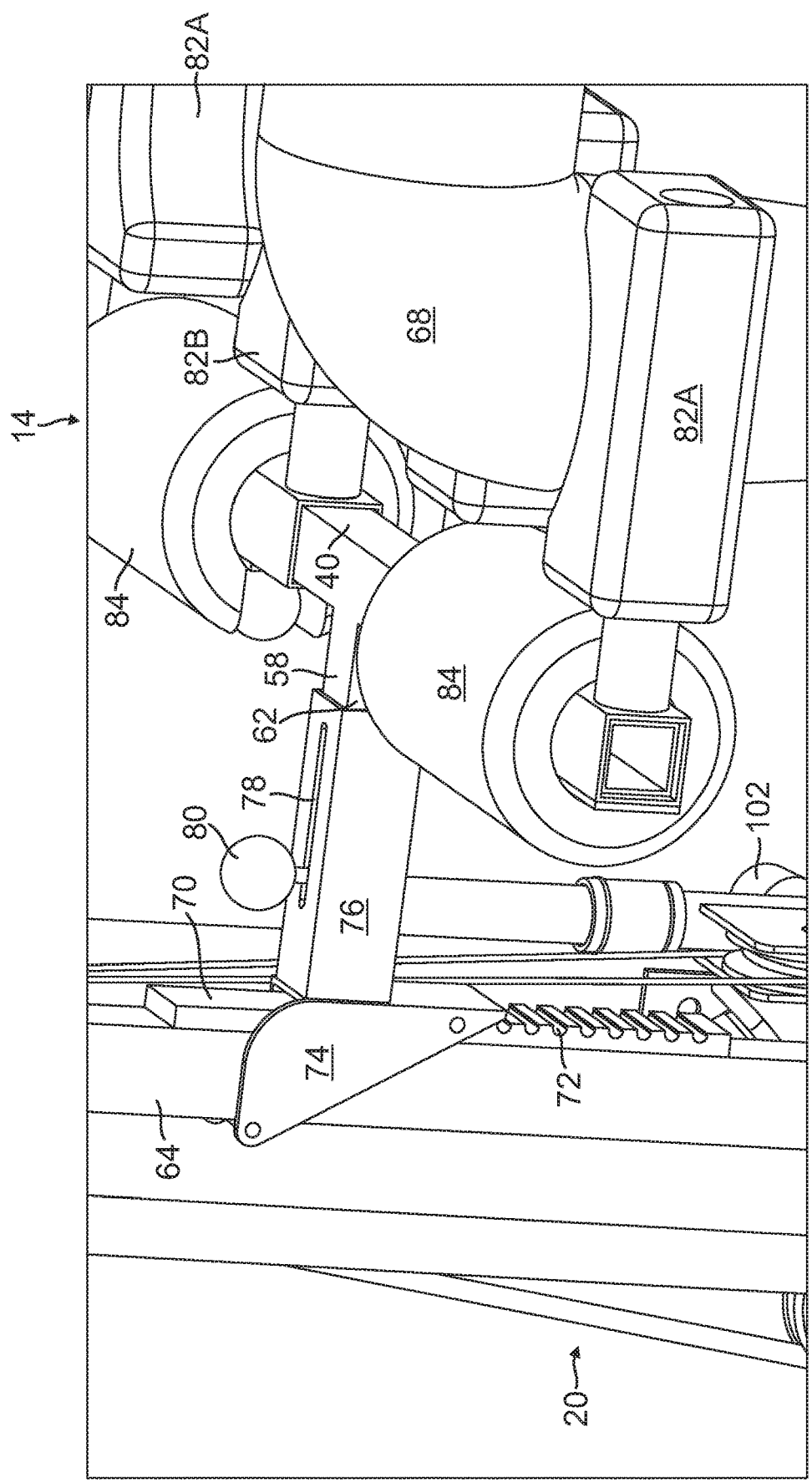
FIG. 7 is a close up view of the attachment portion of the knee support of the apparatus of the instant invention.

Various resistances can be provided using the foot plate system 12. As shown in FIG. 3, pulleys 44A, 44B, 46A, 46B, 48A, 48B, provide for cable wires 50 that can be connected to the foot plates 22. The cable wires 50 are each connected to one of the foot plates 22 and travel upward through pulleys 44A, 44B to pulleys 52A, 52B, and then downward to a second end connected to clips 54. Clips 54 can be connected to resistance tubing 56 (e.g., Cando® tubing), which is connected at a second end to clips. The resistance tubing can be changed as needed to provide different resistances and strengths depending on the user and the exercise. Additional weight in the form of free weight plates can be added to the exercise through extending support bars 102 that extend outward from the machine and that are connected to the pulley system 20.

An example of how a person would use the foot plate system 12 would be unclip the foot strap 30 and ankle strap 32 and place the user's foot onto the sole of the boot 28, clipping the foot strap 30 comfortably over the foot by securing the pin 34 into the hole 36 and repeating with the ankle strap 32. The therapist can then assist the user helping them reach the goal degree. The user would try to rotate the foot plate 22 counterclockwise or clockwise to the desired degree. A second way to use the foot plate system is to begin terminal flicks, which can be done by moving the foot plate 22 clockwise or counterclockwise 5-10 degrees with respect to the base plate 24, and having the user turn the base plate 24 back and forth very quickly from the 5-10 degree point reached and back and forth to the 0 degree, or starting position. This can cause the user to quickly interchange concentric to eccentric contractions to improve motor control function to the muscles. Various resistance tubing can be used to provide different resistances as needed for the different exercises.

The foot plate system 12 can be used in a standing or sitting position. In some exemplary embodiments, when the user is in a sitting position, a knee support 14 can be provided to be used in conjunction with the foot plate system 12. The knee support 14 comprises a support bracket 58, which can have an adjustable height and depth on the exercise apparatus 10. The entire support bracket 58 has a t-shape easily from a top perspective as in FIGS. 4, 11, 12 and 17. The bracket 58 has a first member 60 that extends across the width of the base frame 24 and a second member 62 which is perpendicular to the first member 60 and extends toward the vertical portion of the apparatus 10 and attaches to the center support 64 of the apparatus 10.

Figure 8:
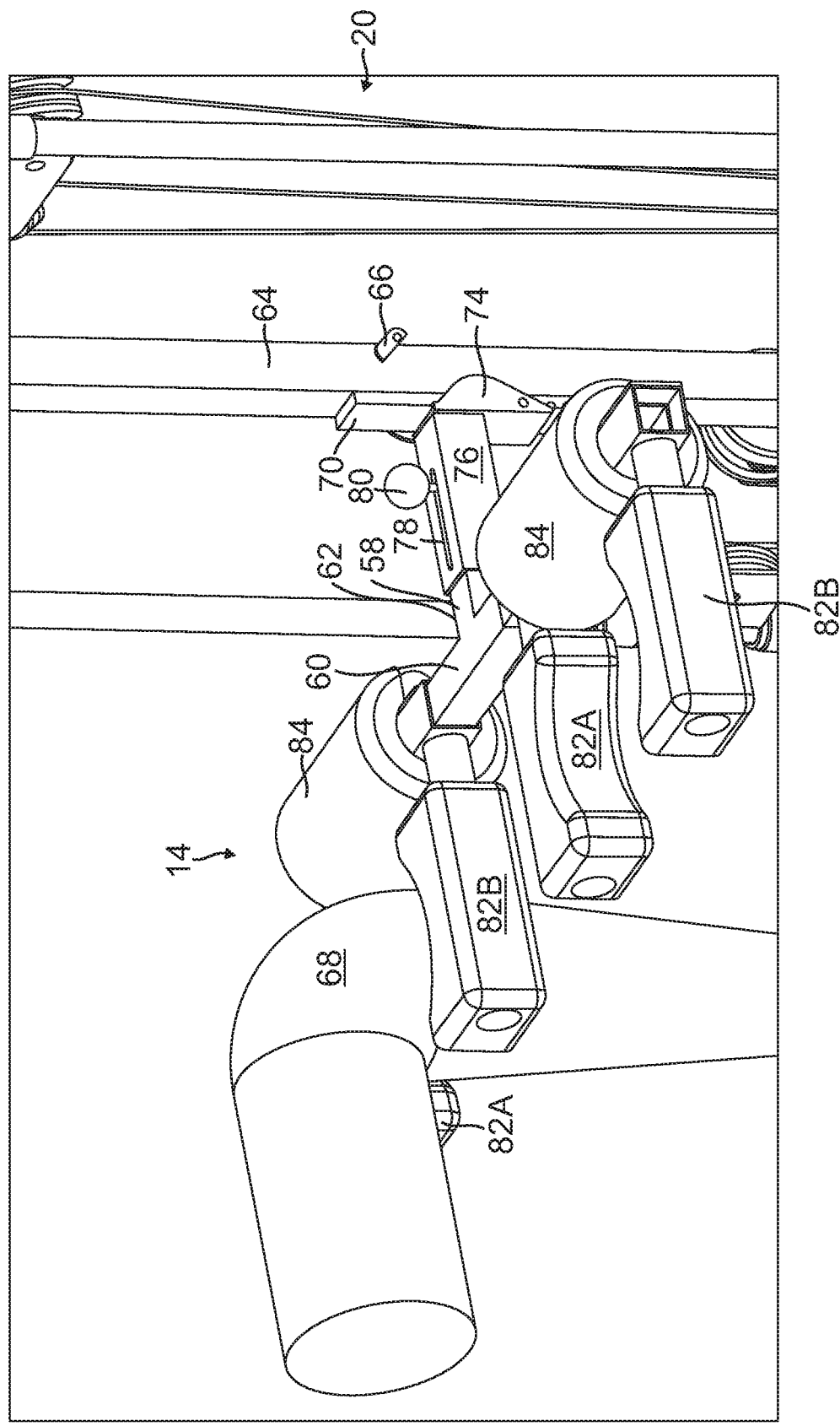
FIG. 8 is a side perspective view of the attachment portion of the knee support of the apparatus of the instant invention.
Figure 9:
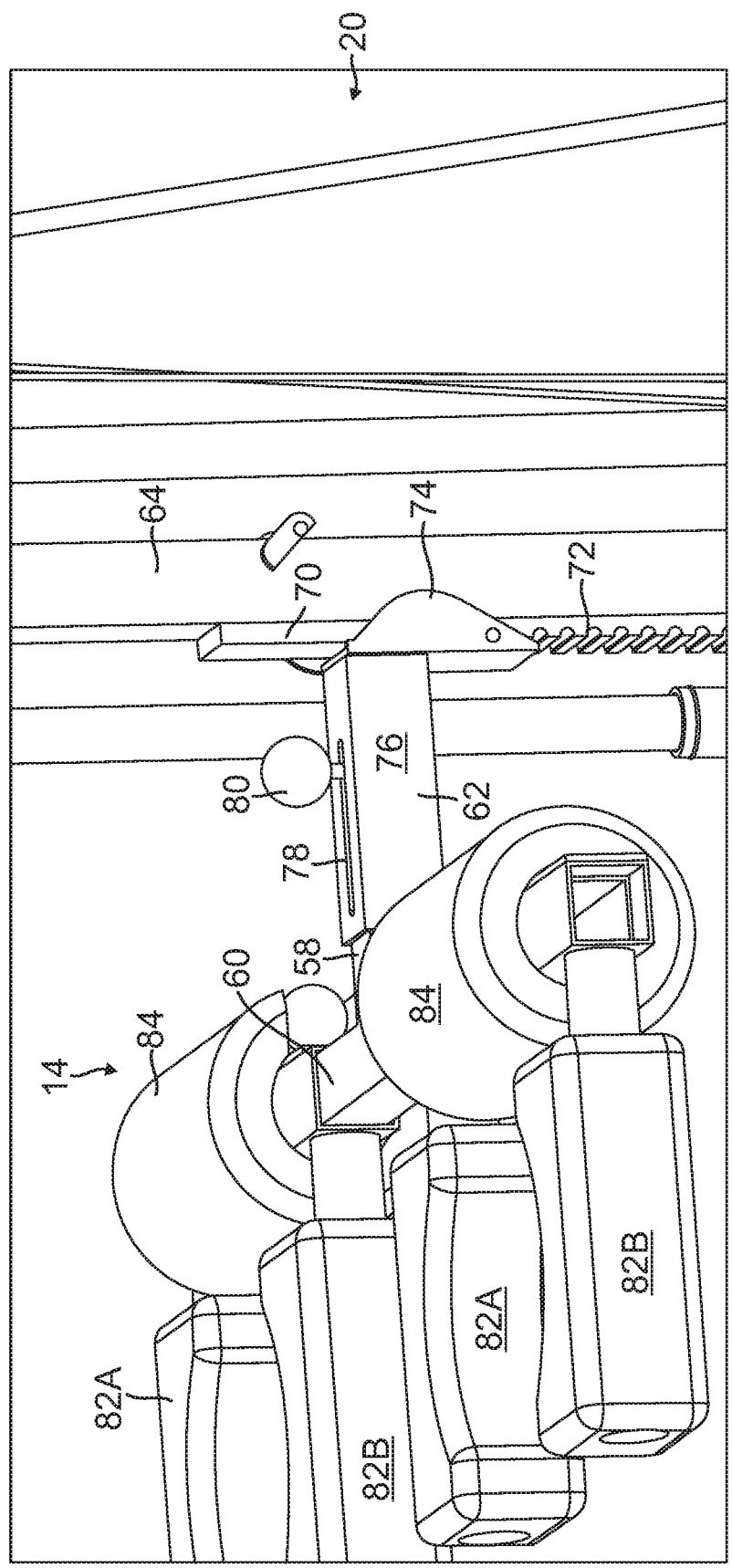
FIG. 9 is a close up side view of the height adjustment portion of the attachment portion of the knee support of the apparatus of the instant invention.
Figure 10:
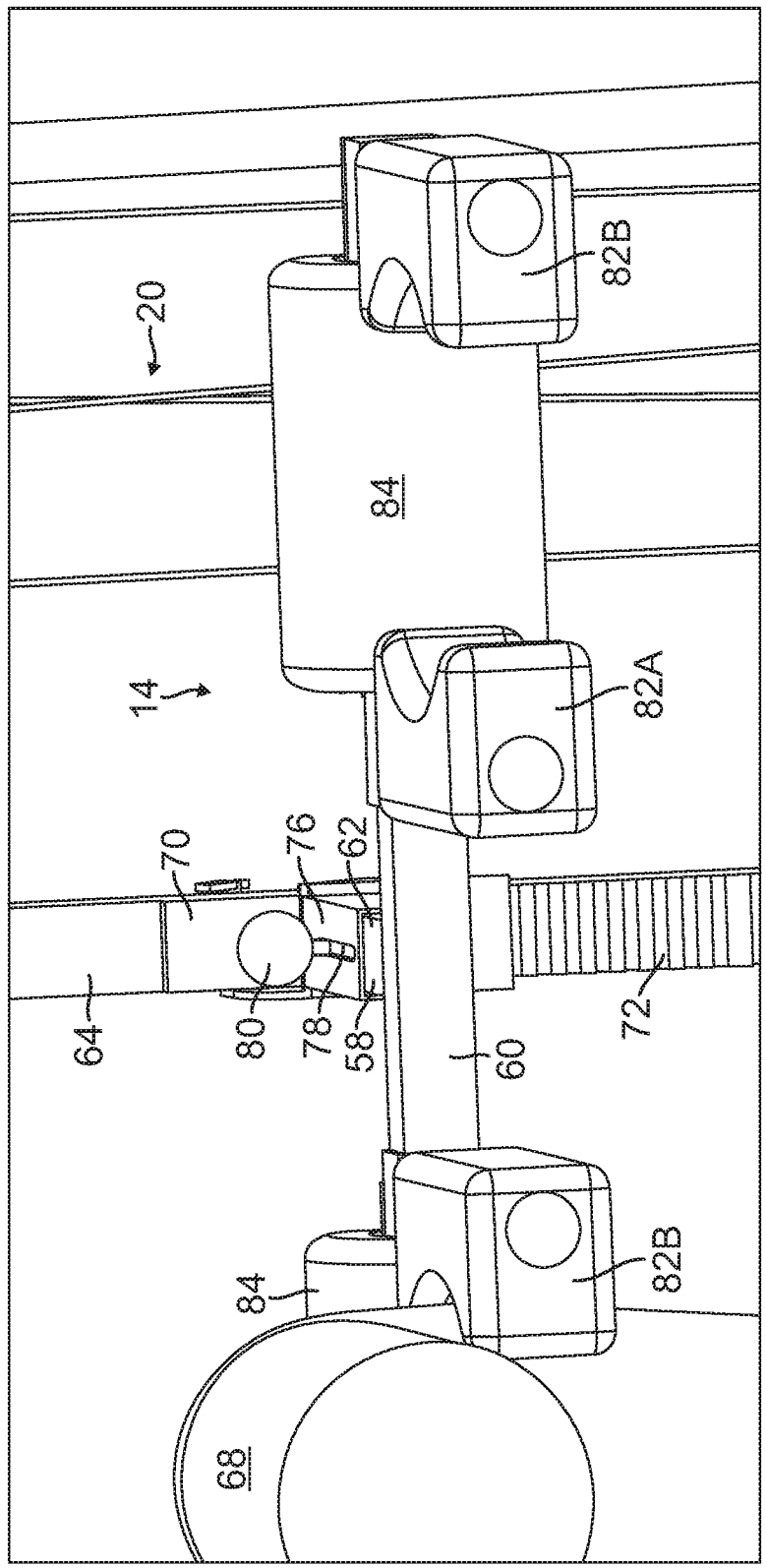
FIG. 10 is a close up front view of the height adjustment portion of the attachment portion of the knee support of the apparatus of the instant invention.
Figure 11:
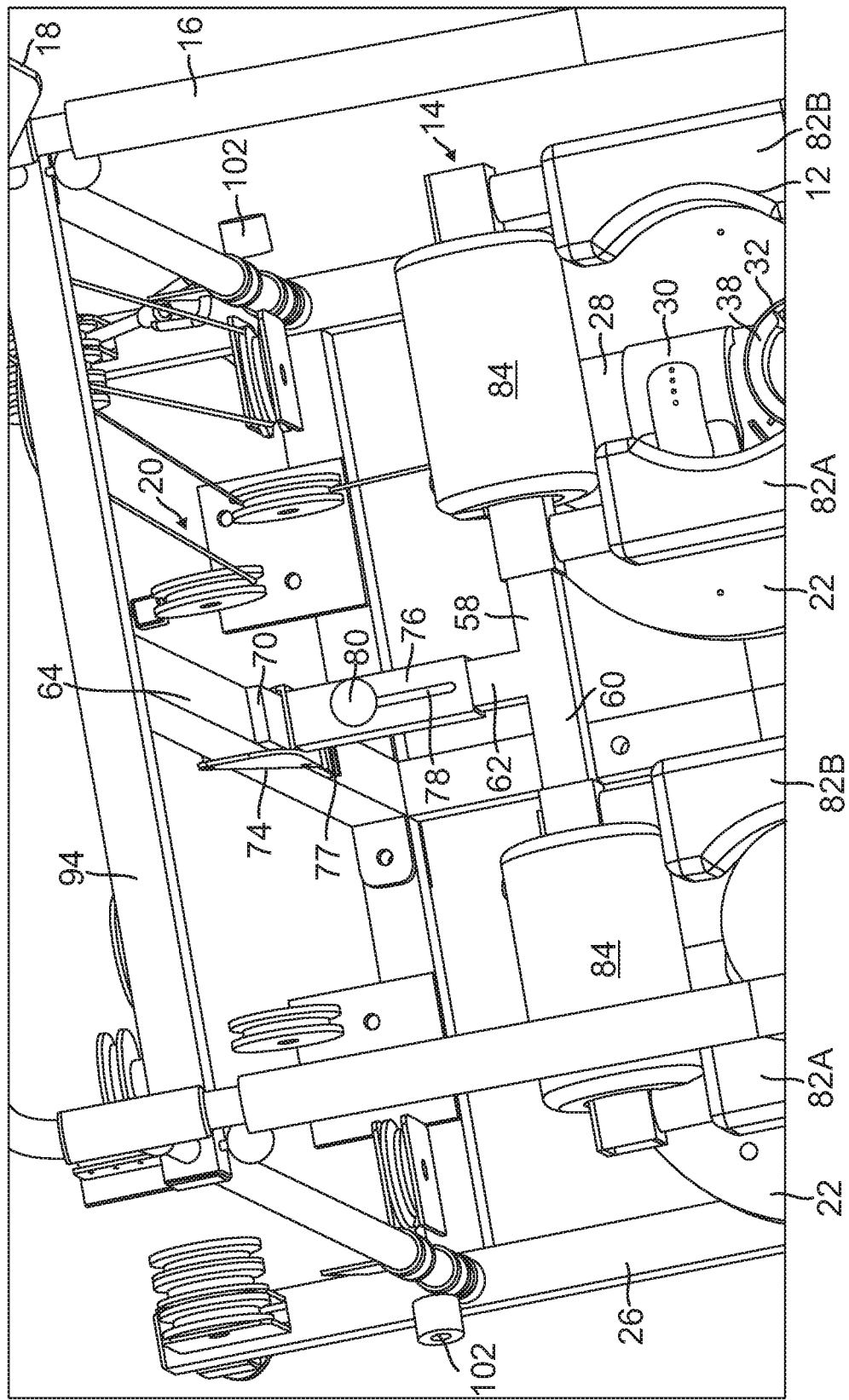
FIG. 11 is a top view of the horizontal adjustment portion of the attachment portion of the knee support of the apparatus of the instant invention.
Figure 12:
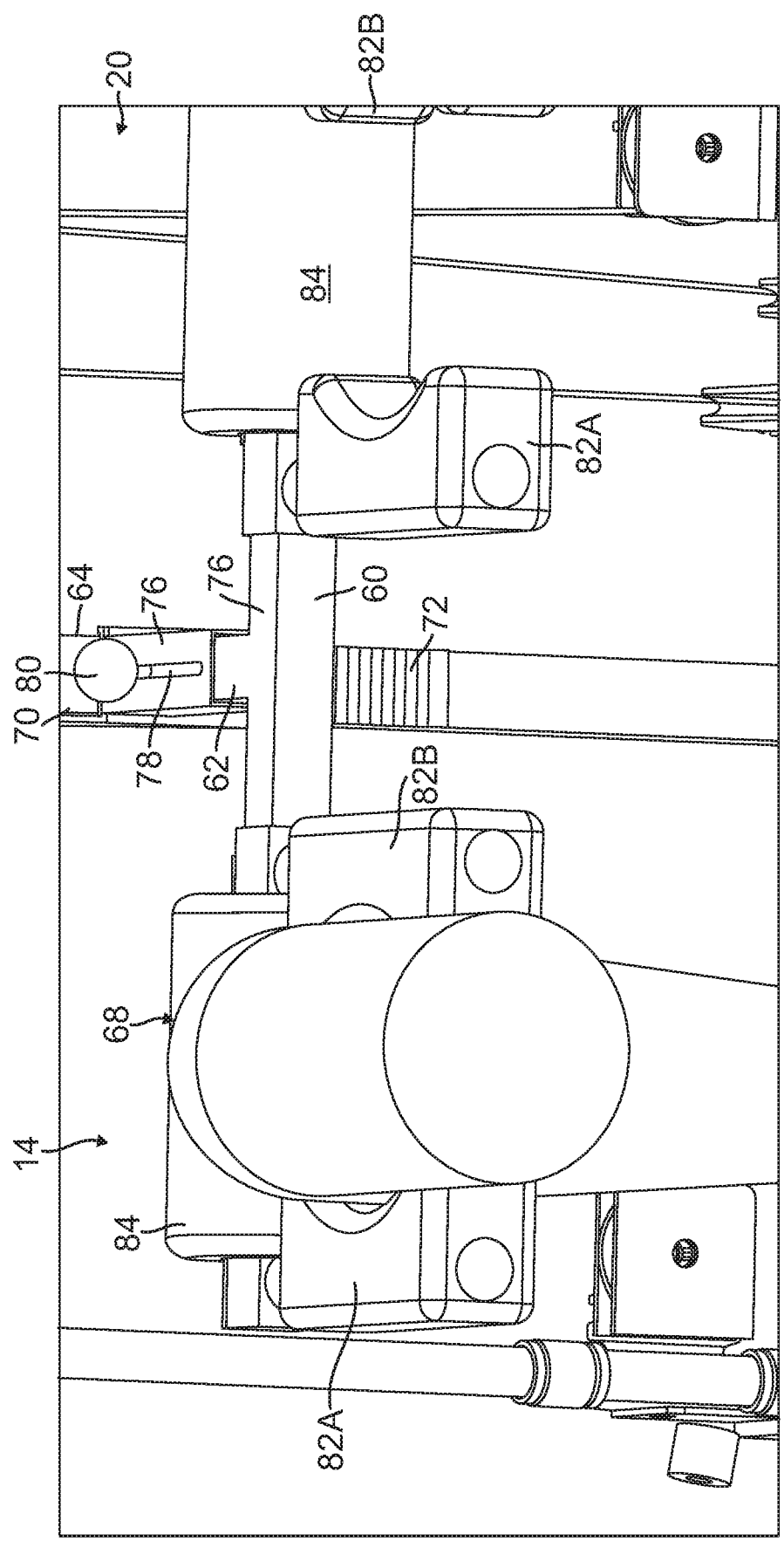
FIG. 12 is a front close up view of the side adjustment mechanism of the knee support of the apparatus of the instant invention.

The knee support bracket 58 is easily removable from the center support 654 and can be set aside when not in use and then re-installed when it is needed. To remove it, the bracket 58 can be pulled up and rotated around a pin 66 in the center support 64 and slid off toward one side. (FIG. 8).

To adjust the height of the knee support bracket 58 relative the height of the user's knee 68. The mechanism for adjusting the height is seen in FIGS. 6-12. Along the center support 64 is affixed a plate 70 with a series of slots 72. The second member 62 of the knee support bracket 60 is removable connected to the plate 70 and held in place with a connection piece 74 between the plate 70 and the second member 62 and is lockable in place to the appropriate height in the appropriate slot 72.

In general operation, the knee supports 58 will support the exercise equipment user at or near the knee 68. The support 58 will be provided by restraining each knee 68 by some degree of horizontal motion, either allowing no horizontal motion of the knee 68, or allowing some amount of horizontal motion in either direction. To achieve this, a movable padded horizontal extension 82A, 82B will be located on each side of each knee 68 or near the knee 68. The padding may or may not be included for the user's comfort as needed.

Each knee support extension 82A, 82B protrudes out from the exercise equipment 10 toward the user in a direction that will be generally parallel to the user's thigh in a seated position. There will be two support extensions 82A, 82B for each knee 68, one for each side of each knee 68, and so four support extensions 82A, 82B total on the exercise equipment 10. The knee support extensions 82A, 82B will be adjustable horizontally to be able to move to and away from each side of each knee 68. These extensions 82A, 82B will be connected, on the ends opposite the user, to a frame 58 so that each knee support 82A, 82B will be adjustable as described. The knee supports 82A, 82B connected to the frame 58 will be one assembled unit. The frame 58 will be connected to the exercise equipment 10 in such a way that allows easy and quick installation and removal of the knee support assembly 14. The frame 58 itself will be adjustable horizontally front to back, toward and away from the user. The frame connection to the exercise equipment will allow vertical adjustment of the knee support assembly. All together, the knee supports 82A, 82B will be adjustable to any position needed by the user.

All of the horizontal adjustments (side-to-side and front-to-back) of the knee support assembly 14 will be by sliding the parts and then fixing them in a location by a spring pin dropping into a hole. There will be a series of holes to allow multiple positions. The spring pin will be the type that is pulled out of the hole by a hand-pull knob. The user pulls the spring pin out, moves the part, then drops the spring pin into the new position.

The vertical positioning of the frame 58 will be done by sliding the frame up and down on the exercise equipment center bar 64 and dropping a pin on the frame into a mating slot on the center bar 64.

As seen in the figures, the knee support bracket 58 is adjustable in the direction toward the apparatus 10 through the adjustment of the second member 62. The second member 62 is surrounded by a cuff 76 with a top slot 78 that is movable through manipulation of a knob 80 that sits inside of the slot 78 and is lockable in various positions in that direction. To adjust, the knob 80 is loosened and moved in and out along that plane.

Figure 13:
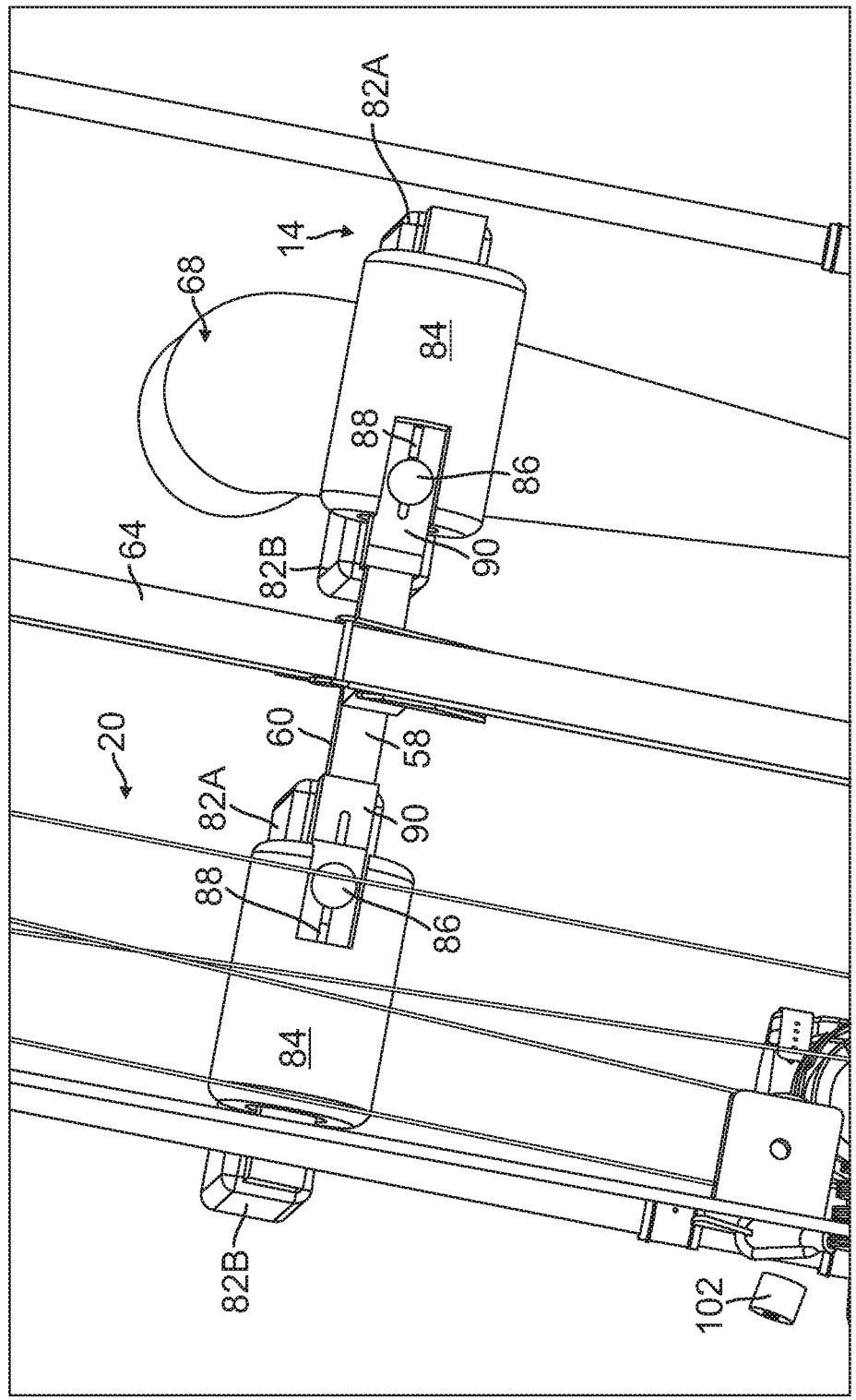
FIG. 13 is a back close up view of the side adjustment mechanism of the knee support of the apparatus of the instant invention.
Figure 14:
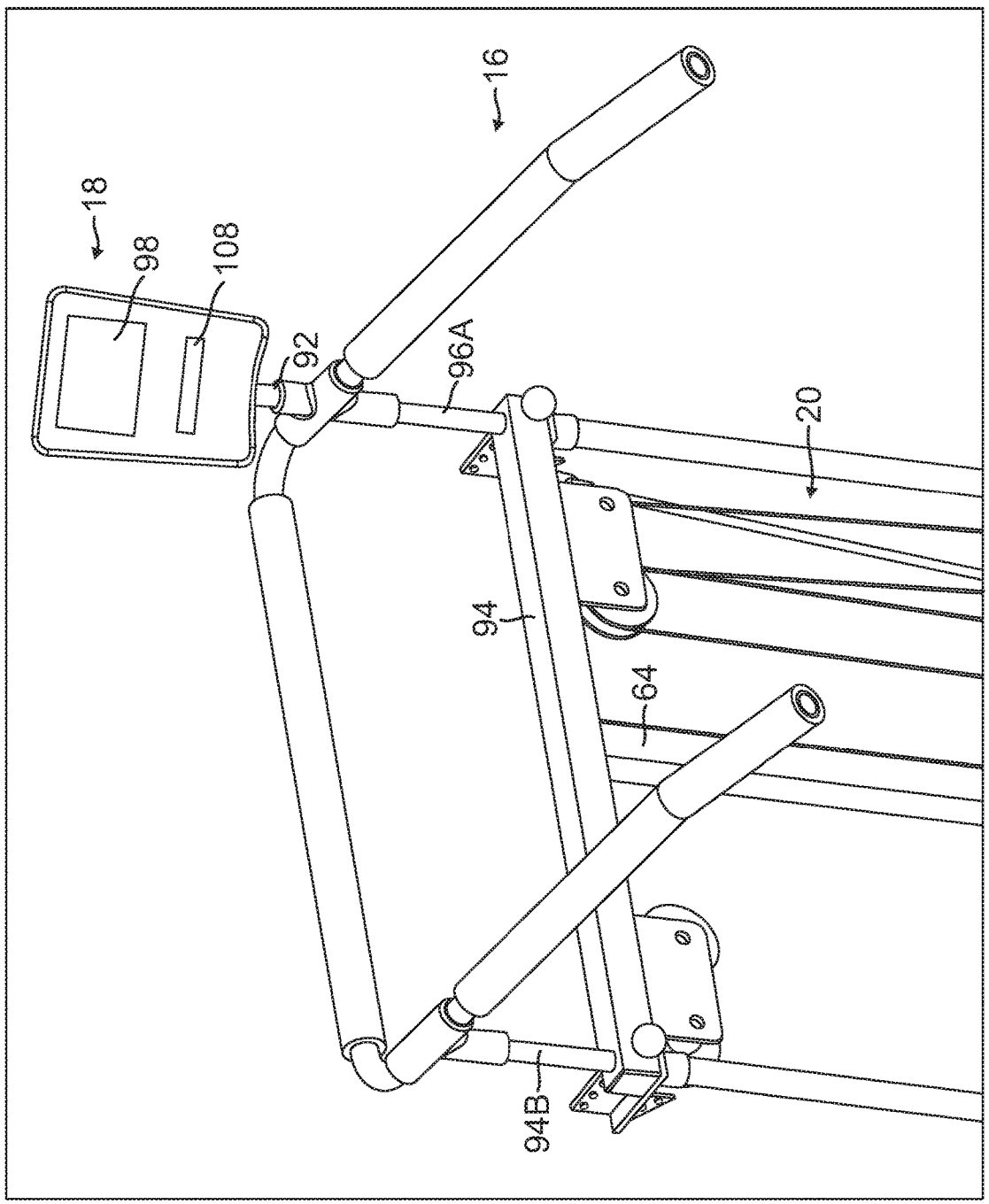
FIG. 14 is a top perspective view of the monitor and handrail of the apparatus of the instant invention.
Figure 15:
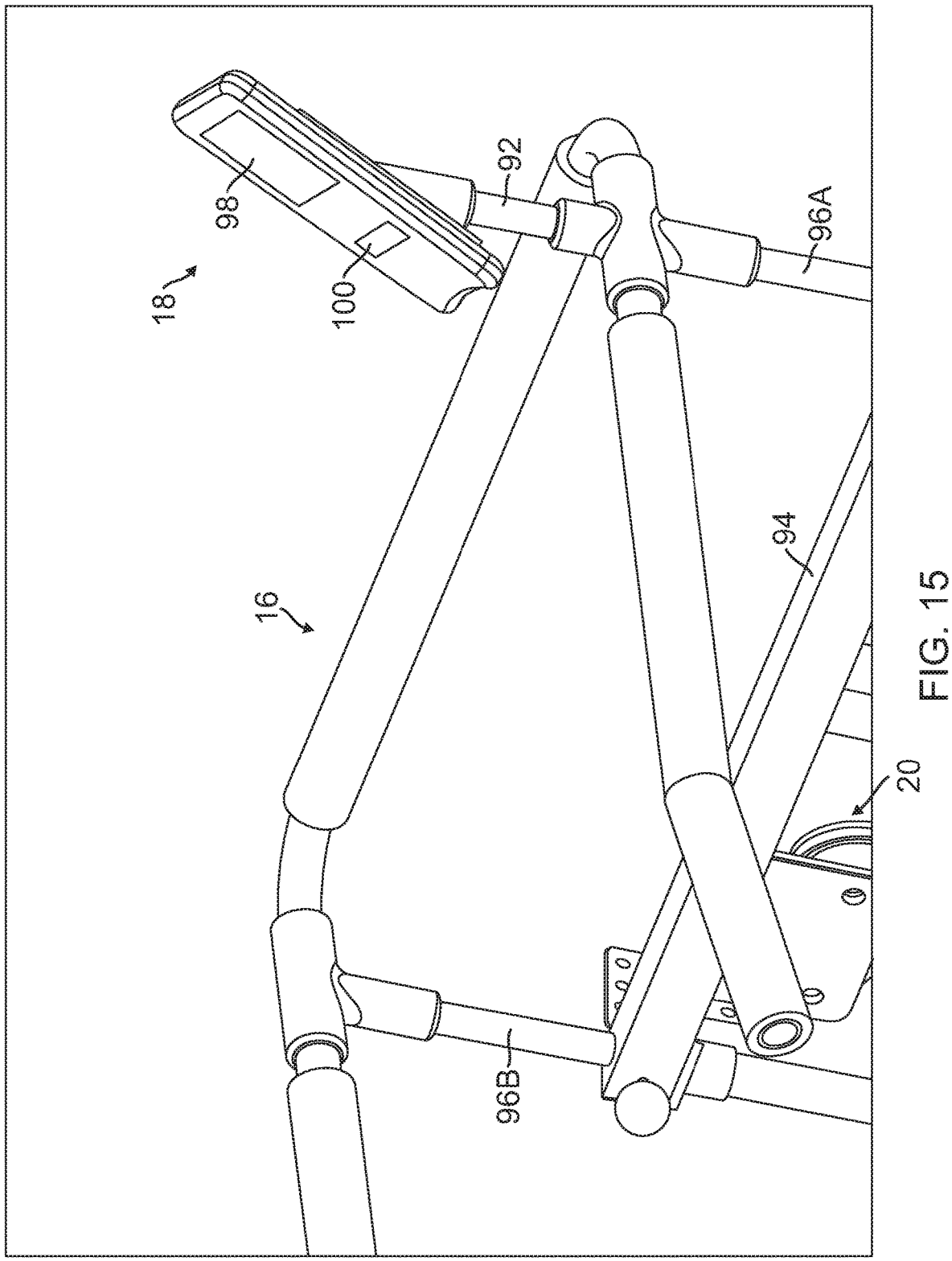
FIG. 15 is a side perspective view of the monitor and handrail of the apparatus of the instant invention.
Figure 16:
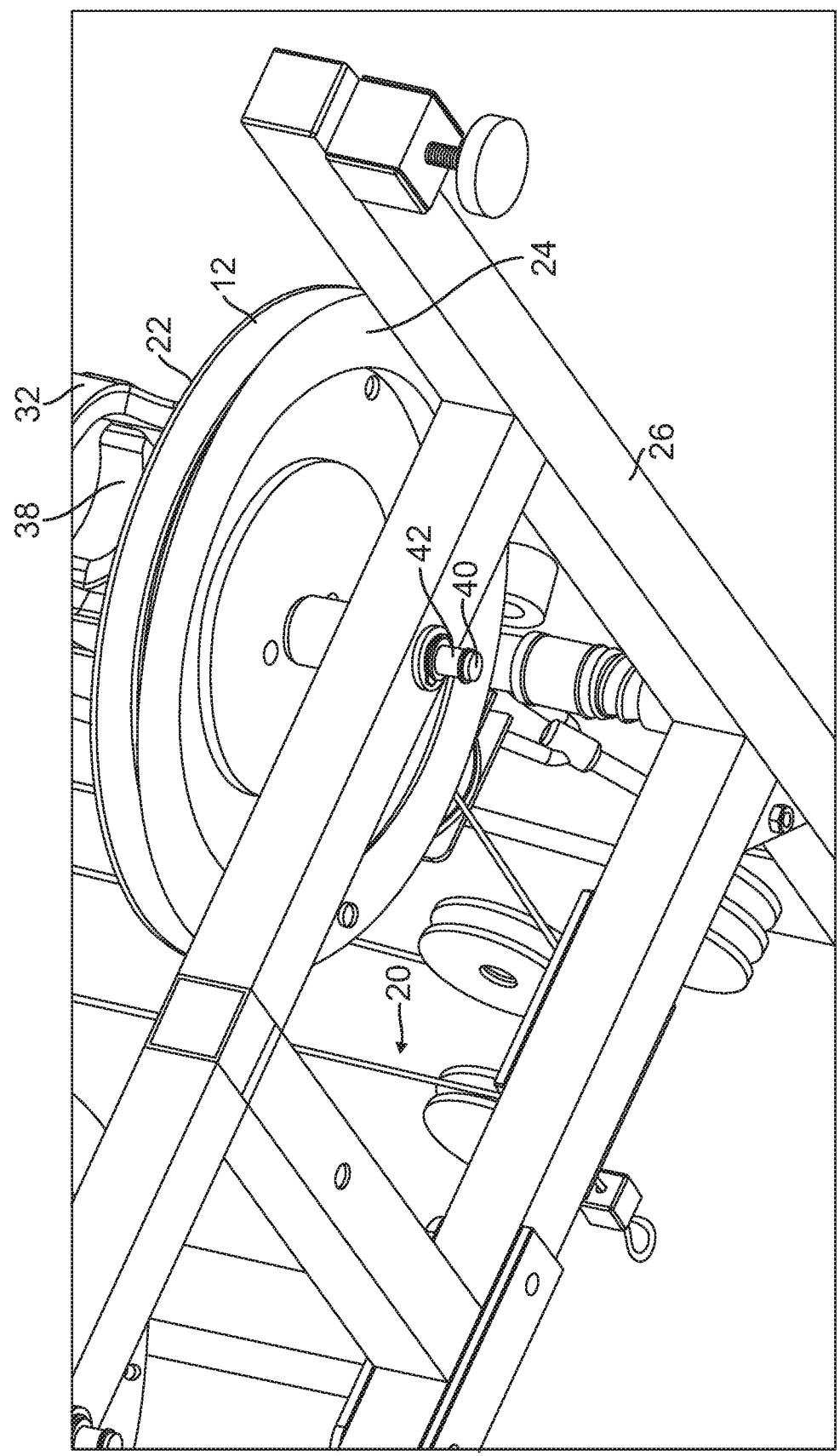
FIG. 16 is a bottom perspective view of the foot plates of the apparatus of the instant invention illustrating the rotational sensors that connect to the monitor of the apparatus of the instant invention.
Figure 17:
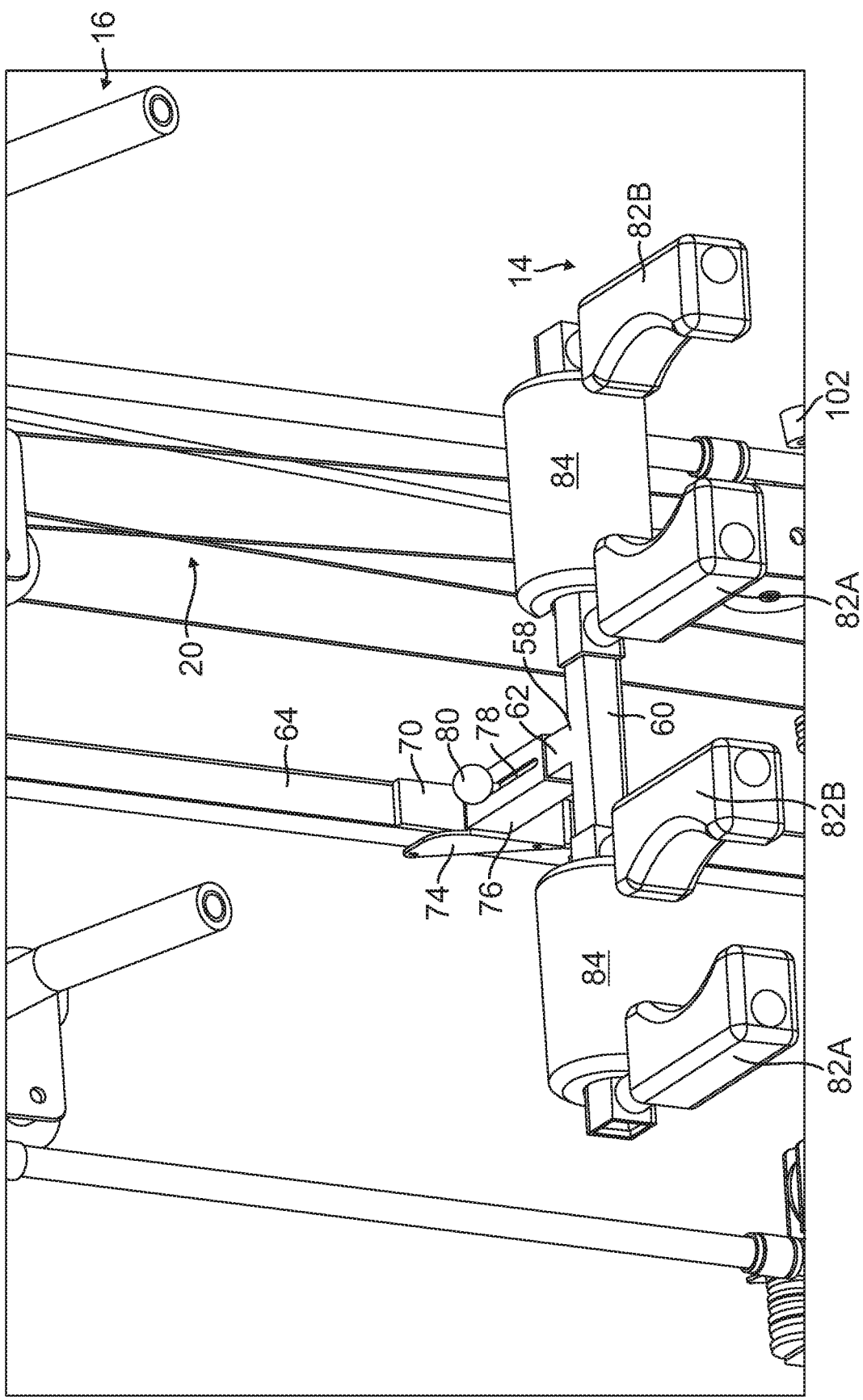
FIG. 17 is a front close up view of the cable wiring of the apparatus of the instant invention where the force sensors are located that send data to the monitor of the apparatus of the instant invention.

As seen in the figures, there is seen the pair of pads 82A, 82B on either side of each knee 68 that are adjustable around the knee 68. These pads are contoured to provide comfort as the pads 82A, 82B enclose the knee 68. Additional support for the knee 68 is also found along the first member 60 of the bracket 82 where pads 84 for each knee 68 are positioned to provide soft support for the front of the knee 68. To adjust the side knee pads 82A, 82B toward the knee, there is a knob 86 on the back of either set of side knee pads 82A, 82B in a slot 88 in a cuff 90 similar to the mechanism for adjusting the bracket 58 back and forth toward the apparatus 10 that allows for the adjustment of the side pads 82A, 82B wherein the inner pad of the pair moves toward the knee 68 thereby providing a comfortable fit for the knee 68. (See FIGS. 3 and 13.)

In use, a user places their knee 68 between the side knee pads 82A, 82B on the support bracket 58 when using the knee support 14 in a sitting position. The knee support 14 can keep the femur from adducting, and provide constant support and stability to the knee 68 thereby allowing a user to isolate internal and external support at the knee 68. By holding the knee 68 in one place in a sitting position, the foot of the user is free to rotate in (inversion) or out (eversion), allowing a therapist to quickly identify compensations at the ankle and lower leg. The knee support 14 can help the user to train the kinetic chain to fire in a certain sequence which helps to reestablish the gate.

A hand rail 16 along the top of the apparatus 10 to provide stability to the user when using it in the standing position. The handrail 16 is typical of what is found on treadmills in that it provides bars to grip in the front of the user and to the side. The hand rail 16 is attached to the top 94 of the apparatus 10 by a pair of posts 96A, 96B that are adjustable in height. The monitor 18 is attached to the hand rail 16 through a post 92 that is also adjustable in height and can also allow the monitor 18 to be rotated around the post 94 so that the trainer can see it or the user can see it, depending on the situation.

The monitor 16 has a readout 98, section and an input section 100 for programming, inputting and receiving data from the machine as the user uses it. The sensors 40 under each foot plate 22 and base plate 24 is in communication with the monitor and provide data thereto. The sensors 40 read the angle of rotation, i.e., how far the foot is turning on the plate and will send that angular data up to the monitor 16.

Additionally, force sensors are included in the cables 50 as they are being pulled, the force sensors measuring how much force is being used for the foot to rotate, to pull the weight up and to pull on the flexible cord. These sensors likewise send this data to the monitor 16.

Various exercises can be performed using the exercise apparatus 10. the back pulley system 20 can be provided at a rear portion of the exercise apparatus 10 as shown in FIG. 3. Pulleys 44A, 44B are provided on upper and lower portions where cable wires are provided through to which various handles can be provided for various exercises.

Various other considerations can also be addressed in the exemplary applications described according to the exemplary embodiments of the present disclosure. For example, various materials may be used to construct the elements described in the figures. Various sizes and dimensions of the apparatus 10 and the parts thereof can be provided. Multiple variations of the pulleys can be provided on the back pulley system 20 and on the exercise apparatus 10 to provide for various exercises and training.

The monitor can provide exercise information and data on the user's workout. Sensors can provide various data on the monitor 16. The sensors can measure resistance and strength in rotational range of motion for the user and trainer, how much weight the user is putting on each foot and which foot is taking more stress. Cameras can be provided to record the user's workout on the various devices of the apparatus 10.

Various advantages can be provided based on the exemplary embodiments described above. For example, the apparatus 10 can allow a user to have an understanding on how to assess, test, analyze and strength train in rotation. A user can quickly achieve the desired strengthening or rehabilitation result they are looking for. The system incorporates the concepts of assessing posture and gait, and a trainer can assist a user in identifying muscle compensations that can occur in the body while training on the apparatus 10. A trainer can teach specific stretches and muscle release techniques to reorganize fascia and reduce muscle tension. Breathing techniques can be incorporated to oxygenate the muscles and to enhance each training session. Following the muscle stretching and tissue release, a user can be taught to strength train on the exercise apparatus. The apparatus 10 allows the user to get the order right by analyzing simple to complex movement patterns. Trainers and users can identify single joint compensations and how to test the individual in a more complex rotational movement pattern. The compensations are documented. Constant resistance keeps the brain engaged throughout the exercises and strengthens key muscle around the ankle, knee, hip and trunk.

The invention illustratively disclosed herein suitably may be practiced in the absence of any element which is not specifically disclosed herein.

The discussion included in this patent is intended to serve as a basic description. The reader should be aware that the specific discussion may not explicitly describe all embodiments possible and alternatives are implicit. Also, this discussion may not fully explain the generic nature of the invention and may not explicitly show how each feature or element can actually be representative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment, a method embodiment, or even merely a variation of any element of these. Particularly, it should be understood that as the disclosure relates to elements of the invention, the words for each element may be expressed by equivalent apparatus terms even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. An exercise apparatus for training and rehabilitation, the exercise apparatus comprising:
    a base frame;
    a vertical support extending upward from said base frame;
    a top frame member attached to said vertical support and being substantially parallel to said base frame;
    a rotating foot system attached to said base frame and comprising:
        a pair of base plates, each base plate affixed to said base frame and respectively configured for each foot of a user;
        a pair of foot plates respectively connected to the pair of base plates;
        at least one strap coupled to each foot plate and configured to respectively secure the feet of the user to the pair of foot plates, said at least one strap securing both a front and a back of said feet of said user;
        a pair of shafts respectively extending downwardly from the pair of foot plates through said base plate; and
        a pair of sensors respectively connected to the pair of shafts, wherein each sensor is configured to detect an angle of rotation data of the respective foot plate when the respective foot plate is rotated by the user;

a pulley system attached to said rotating foot system and including force sensors;

a pair of protruding members connected to said pulley system and respectively extending outward from opposing sides of said exercise apparatus, said pair of protruding members receiving free weights operable to add a first resistance to rotation of said rotating foot system;

resistance tubing connected to said pulley system and operable to add a second resistance to rotation of said rotating foot system;

a knee support system attached to said vertical support that is situated above and substantially parallel to said rotating foot system;

a hand rail attached to said top frame member; and a monitor attached to said hand rail.

2. The exercise apparatus as defined in claim 1 wherein said pair of sensors are configured to respectively sends said angle of rotation data to a processor.

3. The exercise apparatus as defined in claim 2 wherein said processor processes said angle of rotation data to said monitor for display or to an external device.

4. The exercise apparatus as defined in claim 1 wherein said force sensors are included in cables of said pulley system and wherein said force sensors send resistance to data to a processor.

5. The exercise apparatus as defined in claim 4 wherein said processor processes said resistance data sent thereto and then relays the processed resistance data to said monitor or sent to an external device.

6. The exercise apparatus as defined in claim 1 wherein said knee support system further comprises:

a removable bracket having a substantial T-shape with a long member and a short member, the long member being situated above said rotating foot system and substantially parallel thereto, and the short member being perpendicular to said long member and releasably attachable to said vertical support;

a pair of support pads configured to respectively correspond to a front of each knee of a user situated along said long member;

a pair of adjustable pads configured to extend outward from said long member toward each knee of the user such that said pair of adjustable pads respectively surrounds and supports each knee of the user, wherein said pair of adjustable pads are adjustable in a plane toward and away from each knee of the user for support of each knee of the user.

7. The exercise apparatus as defined in claim 6 wherein said pair of adjustable pads are contoured and padded for comfort.

8. The exercise apparatus as defined in claim 6 wherein said removable bracket is adjustable in a vertical direction and configured to accommodate a height of a calf of the user.

9. The exercise apparatus as defined in claim 6 wherein said removable bracket is adjustable in a horizontal direction and configured to accommodate a length of a thigh of the user.

10. The exercise apparatus as defined in claim 1 and configured to accommodate a length of a thigh of the user.

11. The exercise apparatus as defined in claim 1 wherein said monitor is rotatably adjustable 360 degrees so that it can be viewed either by a user or a trainer.

* * * * *